US012779055B2

(12) United States Patent
Mariani et al.

(10) Patent No.: US 12,779,055 B2
(45) Date of Patent: Nov. 3, 2026

(54) PROSTATE SPECIFIC MEMBRANE ANTIGEN (PSMA) LIGANDS AND USES THEREOF

(71) Applicants: ADVANCED ACCELERATOR APPLICATIONS (ITALY) SRL, Pozzilli (IT); THE JOHNS HOPKINS UNIVERSITY, Baltimore, MD (US)

(72) Inventors: Maurizio F. Mariani, Ivrea (IT); Lorenza Fugazza, Ivrea (IT); Daniela Chicco, Pozzilli (IT); Martin Gilbert Pomper, Baltimore, MD (US); Sangeeta Ray, Ellicott City, MD (US)

(73) Assignees: ADVANCED ACCELERATOR APPLICATIONS (ITALY) SRL, Pozzilli (IT); THE JOHNS HOPKINS UNIVERSITY, Baltimore, MD (US)

( * ) Notice: Subject to any disclaimer, the term of this patent is extended or adjusted under 35 U.S.C. 154(b) by 1103 days.

(21) Appl. No.: 17/622,060

(22) PCT Filed: Jun. 30, 2020

(86) PCT No.: PCT/EP2020/068386
§ 371 (c)(1),
(2) Date: Dec. 22, 2021

(87) PCT Pub. No.: WO2021/001360
PCT Pub. Date: Jan. 7, 2021

(65) Prior Publication Data

US 2023/0226227 A1 Jul. 20, 2023

(30) Foreign Application Priority Data

Jul. 2, 2019 (EP) .................................... 19184015

(51) Int. Cl.
*A61K 51/04* (2006.01)
*A61P 35/00* (2006.01)

(52) U.S. Cl.
CPC .......... *A61K 51/0402* (2013.01); *A61P 35/00* (2018.01)

(58) Field of Classification Search
CPC ................................ A61K 51/04; A61P 35/00
See application file for complete search history.

(56) References Cited

U.S. PATENT DOCUMENTS

| | | | | |
|---|---|---|---|---|
| 11,458,213 | B2 * | 10/2022 | Ray | A61P 35/00 |
| 11,478,558 | B2 * | 10/2022 | Ray | A61K 51/0482 |
| 11,813,340 | B2 * | 11/2023 | Pomper | C07F 5/003 |
| 2013/0034494 | A1 * | 2/2013 | Babich | C07D 257/02 534/10 |

FOREIGN PATENT DOCUMENTS

| | | | |
|---|---|---|---|
| WO | WO-2009002529 | A2 | 12/2008 |
| WO | WO-2009026177 | A1 | 2/2009 |
| WO | WO-2010065902 | A2 | 6/2010 |
| WO | WO-2014028057 | A1 | 2/2014 |
| WO | WO-2014110372 | A1 | 7/2014 |
| WO | WO-2015055318 | A1 | 4/2015 |
| WO | WO-2017054907 | A1 | 4/2017 |
| WO | WO-2017070482 | A2 | 4/2017 |
| WO | 2017/165473 | A1 | 9/2017 |
| WO | WO-2018031809 | A1 | 2/2018 |
| WO | 2018/222778 | A1 | 12/2018 |
| WO | 2019/157037 | A1 | 8/2019 |
| WO | 2020/028323 | A1 | 2/2020 |
| WO | WO-2021001360 | A1 | 1/2021 |

OTHER PUBLICATIONS

Jan Tykvart et al. Rational design of urea-based glutamate carboxypeptidase II (GCPII) inhibitors as versatile tools for specific drug targeting and delivery, Bioorg. Med and Chem, 22, 4099-4108. (Year: 2014).*
International Search Report and Written Opinion for International PCT Application No. PCT/EP2020/068386, mailed Sep. 29, 2020 (11 pages).
Lindenberg L., et al., "Safety, Dosimetry, and Feasibility of [68Ga]Ga-PSMA-R2 as an Imaging Agent in Patients with Biochemical Recurrence or Metastatic Prostate Cancer," The Journal of Nuclear Medicine, Mar. 2025, vol. 66, No. 03, pp. 359-365.
Belikov V.G., "Relationship Between the Chemical Structure, Properties of Compounds and Their Action on the Body", Pharmaceutical Chemistry, 2007, chapter 2.6, pp. 27-29.
Cutler C.S., et al., "Radiometals for Combined Imaging and Therapy", Chemical Reviews, vol. 113, 2013, pp. 858-883.
Durnov, et al., "Pediatric Oncology", 2002, p. 139 (3 pages).
Dyson G., et al., "Chemistry of Synthetic Drugs", 1964, pp. 12-19 (22 Pages).
Kratochwil C., et al., "PSMA-Targeted Radionuclide Therapy of Metastatic Castration-Resistant Prostate Cancer with 177Lu-Labeled PSMA-617," Journal of Nuclear Medicine, Aug. 2016, vol. 57, No. 8, pp. 1170-1176 (8 Pages).
Kummerer K., "Pharmaceuticals in the Environment", Annual Review of Environment and Resources, vol. 35, Aug. 18, 2010, pp. 57-75 (22 pages).

* cited by examiner

*Primary Examiner* — Michael G. Hartley
*Assistant Examiner* — Jagadishwar R Samala
(74) *Attorney, Agent, or Firm* — Casimir Jones, SC; Jeffrey W. Childers

(57) ABSTRACT

The present disclosure relates to prostate specific membrane antigen (PSMA) ligands. In particular, the disclosure relates to PSMA ligands having a glutamate-urea-lysine (GUL) moiety and a chelating agent that can comprise a radiometal. The disclosure also relates to the use of these compounds in imaging and in the treatment of prostate cancer.

13 Claims, 3 Drawing Sheets

PROSTATE SPECIFIC MEMBRANE ANTIGEN (PSMA) LIGANDS AND USES THEREOF

GOVERNMENT SUPPORT CLAUSE

This invention was made with government support under EB024495, CA184228, CA148901 and CA134675, awarded by the National Institutes of Health. The government has certain rights in the invention.

TECHNICAL FIELD

The present disclosure relates to prostate specific membrane antigen (PSMA) ligands. In particular, the disclosure relates to PSMA ligands having a glutamate-urea-lysine (GUL) moiety and a chelating agent that can comprise a radiometal.

The disclosure also relates to the use of these compounds in imaging and in the treatment of prostate cancer.

BACKGROUND ART

Prostate cancer is one of the most widespread cancers in the US and in Europe. In particular, metastatic prostate cancer (mCRPC) is associated with poor prognosis and diminished quality of life.

Recently, a new development stream for treating prostate cancer is represented by the endo-radiotherapy based on PSMA ligands, as PSMA is considered to be a suitable target for imaging and therapy due to its over-expression in primary cancer lesions and in soft-tissue/bone metastatic disease. Also, PSMA expression seems to be even higher in the most aggressive castration-resistant variants of the disease, which represents a patient population with high unmet medical need. (Marchal et al., Histol Histopathol, 2004 July; 19(3):715-8; Mease et al., Curr Top Med Chem, 2013, 13(8):951-62).

Among many small-molecule ligands targeting PSMA, the urea-based low molecular weight agents have been the most extensively investigated ones. These agents were shown to be suitable for prostate cancer clinical assessment as well as for PRRT therapy (Kiess et al., Q J Nucl Med Mol Imaging, 2015; 59:241-68). Some of these agents have glutamate-urea-lysine (GUL) as the targeting scaffold. A class of molecules was created following the strategy to attach a linker between the chelator and GUL moiety. This approach allows the urea to reach the binding site while keeping the metal chelated portion on the exterior of the binding site. This strategy was successful in xenograft PSMA positive tumors due to its demonstrated high uptake and retention as well as fast renal clearance (Banerjee et al., J Med Chem, 2013; 56:6108-21).

However, some of these compounds still show a high uptake in different organs, like the kidneys, which can induce toxicity in human patients. Thus, it is desirable to develop new PSMA ligands having low uptake in different organs.

SUMMARY OF THE DISCLOSURE

In a first aspect, the present disclosure relates to compounds of formula (I):

(I)

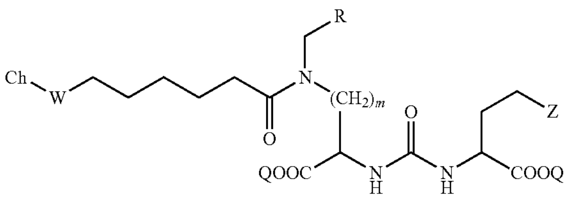

wherein:

Z is tetrazole or COOQ, preferably Z is COOQ;

Q is H or a protecting group, preferably Q is H;

m is an integer selected from the group consisting of 1, 2, 3, 4, and 5, preferably m is 4; R is selected from the group consisting of substituted aryl, substituted pyridine, and unsubstituted isoquinoline;

W is selected from the group consisting of —$NR^2$—(C═O), —$NR^2$—(C═S), —(C═O)—$NR^2$—, and —(C═S)—$NR^2$—, preferably, W is —(C═O)—$NR^2$—;

$R^2$ is H or C1-C4 alkyl, preferably $R^2$ is H;

Ch is a chelating agent optionally comprising a metal or a radiometal;

and pharmaceutically acceptable salts thereof.

The linker between the glutamate-urea-lysine (GUL) moiety and the chelating agent Ch comprises a $C_5$-alkyl chain, which enables a lower uptake of the radiolabeled molecule in different organs, while having a good tumor-to-kidney ratio. This low uptake indicates a decreased toxicity in human patients for these types of molecules. Moreover, the high tumor-to-kidney ratio suggests a good visualization of the tumor, when used in imaging.

In a second aspect, the disclosure relates to a pharmaceutical composition comprising a compound of formula (I) and at least one pharmaceutically acceptable carrier.

In a third aspect, the disclosure relates to a compound of formula (I) for use as a medicament.

In a fourth aspect, the disclosure relates to a compound of formula (I), for use in treating cancer, especially prostate cancer.

In a fifth aspect, the disclosure relates to a compound of formula (I), for use in imaging.

In a sixth aspect, the disclosure also relates to a method for treating prostate cancer, the method comprising contacting the cancer cells with an effective amount of the compound of formula (I).

In a seventh aspect, the disclosure also relates to a method for imaging, the method comprising contacting the cancer cells with an effective amount of the compound of formula (I).

DETAILED DESCRIPTION

Definitions

Figure 1:
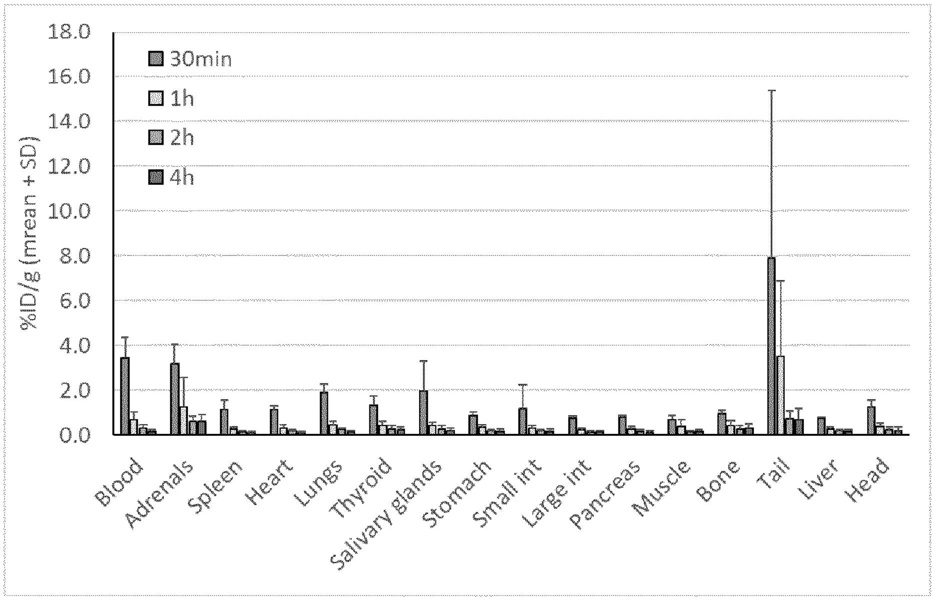
FIG. 1 shows the $^{68}$Ga-PSMA-R2 biodistribution in healthy CD-1 mice (Mean values ±SD) according to example 1.

As used herein, the term "protecting group" in reference to compounds of formula (I) refers to a chemical substituent which can be selectively removed by readily available reagents which do not attack the regenerated functional group or other functional groups in the molecule. Suitable protecting groups are known in the art and continue to be developed. Suitable protecting groups may be found, for example in Wutz et al. ("Greene's Protective Groups in Organic Synthesis, Fourth Edition," Wiley-Interscience, 2007). Protecting groups for protection of the carboxyl group, as described by Wutz et al. (pages 533-643), are used in certain embodiments. In some embodiments, the protecting group is removable by treatment with acid.

Representative examples of protecting groups include, but are not limited to, benzyl, p-methoxybenzyl (PMB), tertiary butyl (t-Bu), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr). Persons skilled in the art will recognize appropriate situations in which protecting groups are required and will be able to select an appropriate protecting group for use in a particular circumstance.

As used herein, the term "aryl" refers to a polyunsaturated, aromatic hydrocarbyl group having a single ring or multiple aromatic rings fused together, containing 6 to 10 ring atoms, wherein at least one ring is aromatic. The aromatic ring may optionally include one to two additional rings (cycloalkyl, heterocyclyl or heteroaryl as defined herein) fused thereto. Suitable aryl groups include phenyl, naphtyl and phenyl ring fused to a heterocyclyl, like benzopyranyl, benzodioxolyl, benzodioxanyl and the like.

As used herein, the terms "substituted aryl" and "substituted pyridine" refer to an aryl as defined above or a pyridine which is substituted by one or more substituents selected from: halogen, —OR', —NR'R'', —SR', —SiR'R''R''', —OC(O)R', —C(O)R', —$CO_2$R', —C(O)NR'R'', —OC(O)NR'R'', —NR''C(O)R', —NR'—C(O)NR''R''', —NR''C(O)OR', —NR—C(NR'R''R''')═NR'''', —NR—C(NR'R'')═NR''', —S(O)R', —S$(O)_2$R', —S$(O)_2$NR'R'', —NR$SO_2$R', —CN, —$NO_2$, —R', —$N_3$, —CH$(Ph)_2$, fluoro($C_1$-$C_4$)alkoxo, and fluoro($C_1$-$C_4$)alkyl, in a number ranging from zero to the total number of open valences on aromatic ring system; and where R', R'', R''' and R'''' may be independently selected from hydrogen, alkyl, heteroalkyl, cycloalkyl, heterocycloalkyl, aryl and heteroaryl. When a compound of the disclosure includes more than one R group, for example, each of the R groups is independently selected as are each R', R'', R''' and R'''' groups when more than one of these groups is present.

As used herein, the term "alkyl", by itself or as part of another substituent, refers to a linear or branched alkyl functional group having 1 to 6 carbon atoms. Suitable alkyl groups include methyl, ethyl, n-propyl, i-propyl, n-butyl, i-butyl, s-butyl and t-butyl, pentyl and its isomers (e.g. n-pentyl, iso-pentyl), and hexyl and its isomers (e.g. n-hexyl, iso-hexyl).

As used herein, the term "heteroalkyl" refers to a linear or branched alkyl functional group having 1 to 6 carbon atoms and from one to three, heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule.

As used herein, the term "cycloalkyl" refers to a saturated or unsaturated cyclic group having 3 to 6 carbon atoms. Suitable cycloalkyl groups include cyclopropyl, cyclobutyl, cyclopentyl and cyclohexyl.

As used herein, the term "halogen" refers to a fluoro (—F), chloro (—Cl), bromo (—Br), or iodo (—I) group.

As used herein, the term "alkoxy" refers to a —O-alkyl group, wherein the alkyl group is a $C_1$-$C_6$ alkyl as defined herein. Suitable alkoxy groups include methoxy, ethoxy, propoxy.

As used herein, the term "heteroaryl" refers to a polyunsaturated, aromatic ring system having a single ring or multiple aromatic rings fused together or linked covalently, containing 5 to 10 atoms, wherein at least one ring is aromatic and at least one ring atom is a heteroatom selected from N, O and S. The nitrogen and sulfur heteroatoms may optionally be oxidized and the nitrogen heteroatoms may optionally be quaternized. Such rings may be fused to an aryl, cycloalkyl or heterocyclyl ring. Non-limiting examples of such heteroaryl, include: furanyl, thiophenyl, pyrrolyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, indolyl, isoindolyl, benzofuranyl, isobenzofuranyl, benzothiophenyl, isobenzothiophenyl, indazolyl, benzimidazolyl, benzoxazolyl, purinyl, benzothiadiazolyl, quinolinyl, isoquinolinyl, cinnolinyl, quinazolinyl and quinoxalinyl.

As used herein, the terms "heterocyclyl" or "heterocylcoalkyl" refer to a saturated or unsaturated cyclic group having 5 to 10 ring atoms, wherein at least one ring atom is a heteroatom selected from N, O and S. The nitrogen and sulfur heteroatoms may optionally be oxidized and the nitrogen heteroatoms may optionally be quaternized. Examples of heterocycle include, but are not limited to, tetrahydropyridyl, piperidinyl, morpholinyl, tetrahydrofuranyl, tetrahydrothienyl, piperazinyl, 1-azepanyl, imidazolinyl, 1,4-dioxanyl and the like.

Various embodiments of the disclosure are described herein. It will be recognized that features specified in each embodiment may be combined with other specified features to provide further embodiments.

The present disclosure encompasses the compounds of formula (I), (II), (III) and (IV), their stereoisomers, tautomers, enantiomers, diastereomers, racemates or mixtures thereof, and their hydrates, solvates or pharmaceutically acceptable salts.

The terms "pharmaceutically acceptable salts" refers to salts that retain the biological effectiveness and properties of the compounds of this disclosure and, which typically are not biologically or otherwise undesirable.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

As used herein the term "subject" refers to an animal, preferably a mammal and more preferably a human.

Compounds of Formula (I)

In a first aspect, the present disclosure relates to compounds of formula (I):

(I)

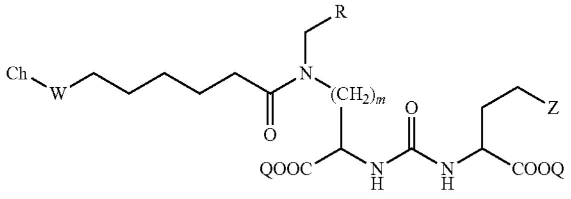

wherein:

Z is tetrazole or COOQ, preferably Z is COOQ;

Q is H or a protecting group, preferably Q is H;

m is an integer selected from the group consisting of 1, 2, 3, 4, and 5, preferably m is 4;

R is selected from the group consisting of substituted aryl, substituted pyridine, and unsubstituted isoquinoline;

W is selected from the group consisting of —$NR^2$—(C═O), —$NR^2$—(C═S), —(C═O)—$NR^2$—, and —(C═S)—$NR^2$—, preferably, W is —(C═O)—$NR^2$—;

$R^2$ is H or $C_1$-$C_4$ alkyl, preferably $R^2$ is H;

Ch is a chelating agent optionally comprising a metal or a radiometal;

and pharmaceutically acceptable salts thereof.

Compounds of formula (I) include the stereoisomers of formulae (Ia), (Ib), (Ic) and (Id):

(Ia)

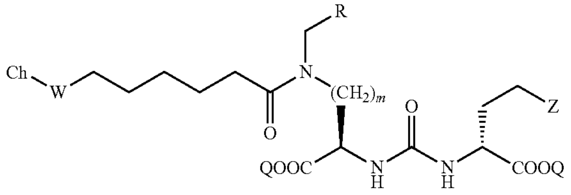

(Ib)

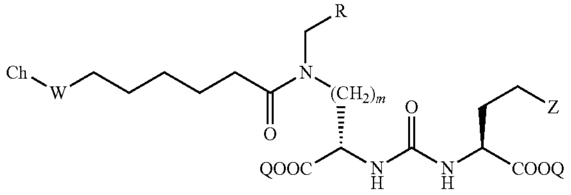

(Ic)

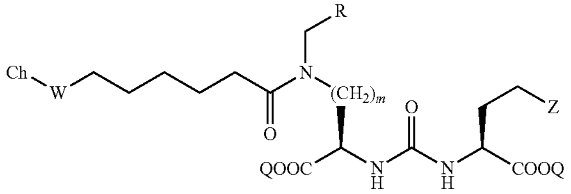

-continued (Id)

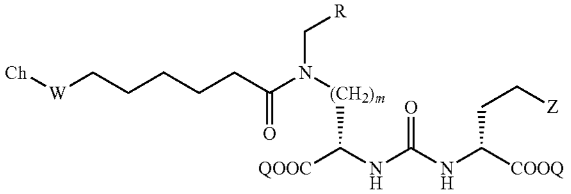

According to an embodiment, R is selected from the group consisting of aryl substituted with one or more halogen, pyridine substituted with one or more halogen, and unsubstituted isoquinoline.

According to a specific embodiment, R is selected from the group consisting of:

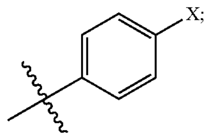

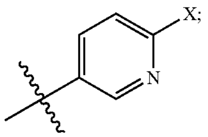

and

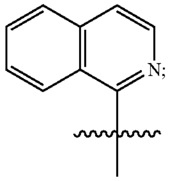

wherein X is independently Br or I.

Advantageously, R is

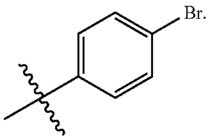 [SMILES: *c1ccc(Br)cc1]

Ch can be selected from the group consisting of:

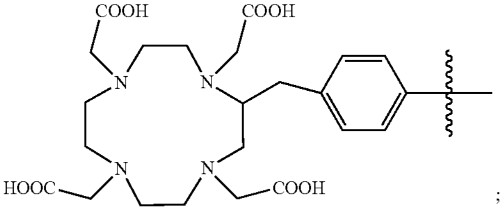

;

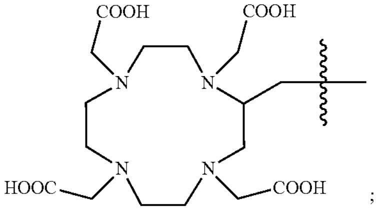

;

-continued

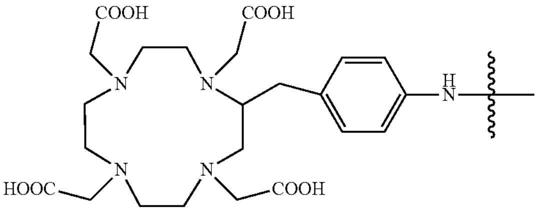

;

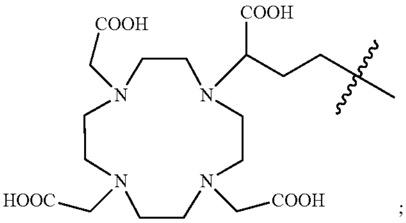

;

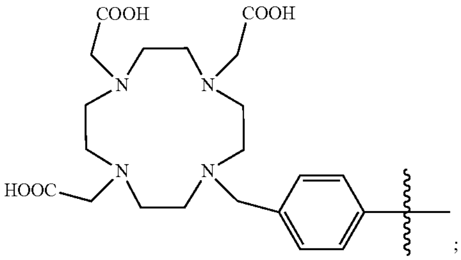

; and

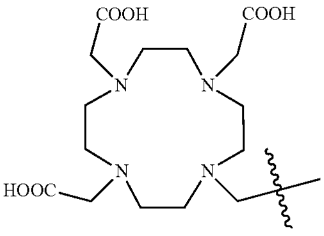

;

and optionally comprises a metal or a radiometal.

According to a specific embodiment, Ch is

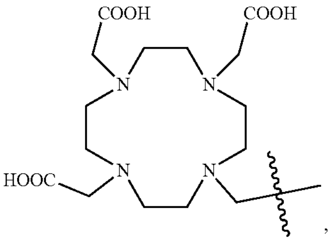 [SMILES: *CN1CCN(CC(=O)O)CCN(CC(=O)O)CCN(CC(=O)O)CC1]

, and optionally comprises a metal or a radiometal.

The metal or radiometal is preferably chosen from metals and radiometals that are suitable for use in imaging method or in therapy.

According to an embodiment, Ch comprises a metal selected from Y, Lu, Tc, Zr, In, Sm, Re, Cu, Pb, Ac, Bi, Al, Ga, Re, Ho and Sc. The metal can be a radiometal selected from $^{68}Ga$, $^{64}Cu$, $^{86}Y$, $^{90}Y$ $^{89}Zr$, $^{111}In$, $^{99m}Tc$, $^{177}Lu$, $^{153}Sm$, $^{186}Re$, $^{188}Re$, $^{67}Cu$, $^{212}Pb$, $^{225}Ac$, $^{213}Bi$, $^{212}Bi$, $^{212}Pb$, $^{67}Ga$ $^{203}Pb$, $^{47}Sc$, and $^{166}Ho$.

Advantageously, Ch comprises a radiometal $^{68}Ga$ or $^{177}Lu$ or $^{225}Ac$.

The compound of formula (I) can be distributed in the body of a tumor bearing animal or human in such a way that, 1 h after the intravenous injection of the compound, the tumor-to-kidney ratio is at least 5 (mean value of at least N=4).

According to an embodiment, W is —(C═O)—$NR^2$—, and Ch is

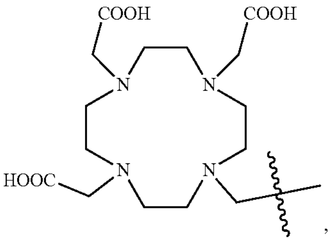 [SMILES: *CN1CCN(CC(=O)O)CCN(CC(=O)O)CCN(CC(=O)O)CC1]

, and optionally comprises a metal or a radiometal.

According to an embodiment, m is 4, Z is COOQ, and Q is H.

According to a specific embodiment, the compound of formula (I) is the compound of formula (II):

(II)

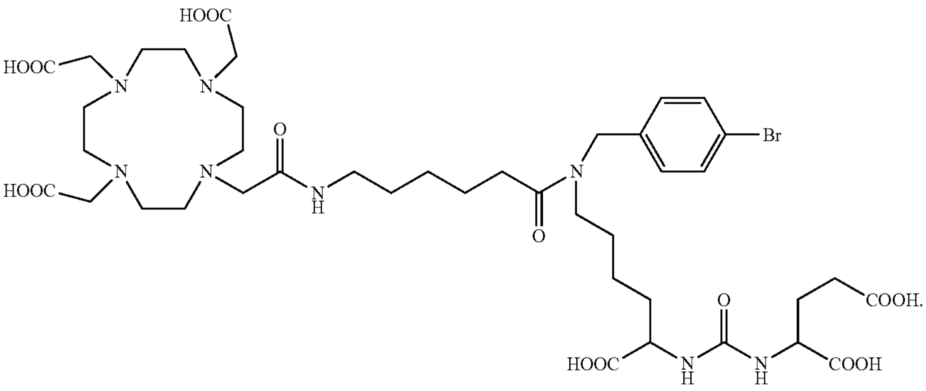

.

The compound of formula (II) can be called PSMA-R2. The compound of formula (II) can comprise a metal or a radiometal, preferably $^{68}Ga$ or $^{177}Lu$.

According to an embodiment, the compound of formula (I) is the compound of formula (III):

(II)

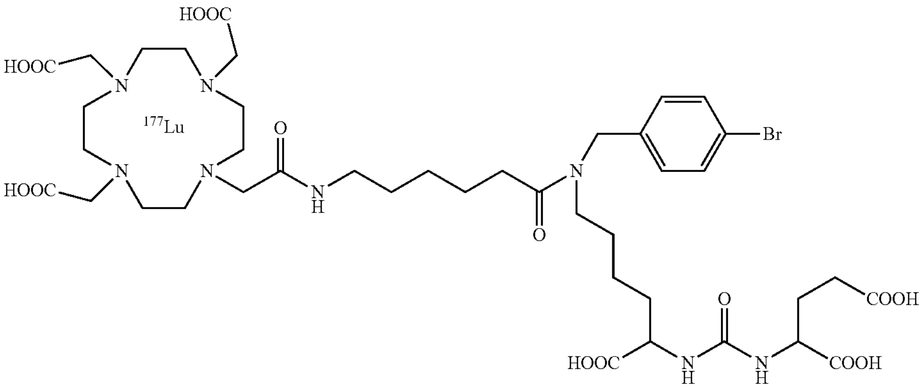

The compound of formula (III) can be called $^{177}Lu$-PSMA-R2. Compounds of formula (III) include the stereoisomers of formulae (IIIa), (IIIb), (IIIc) and (IIId):

(IIIa)

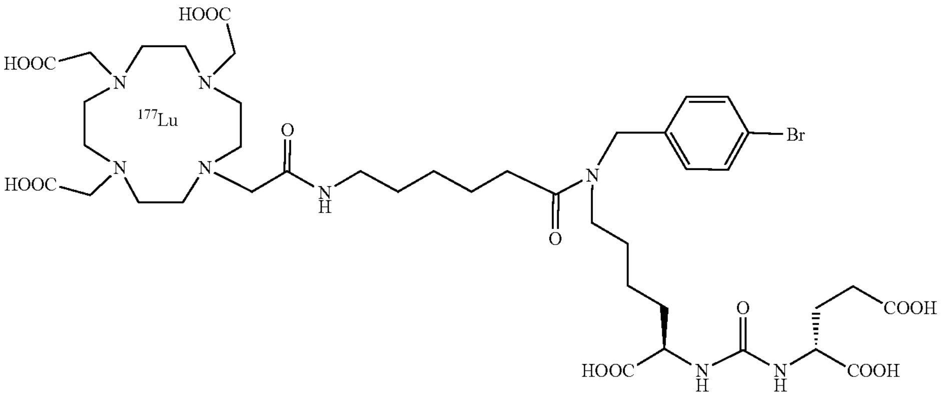

(IIIb)

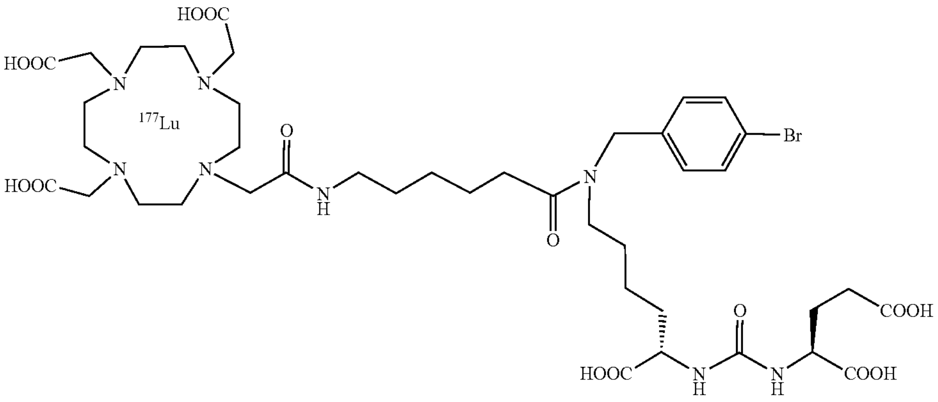

-continued
(IIIc)
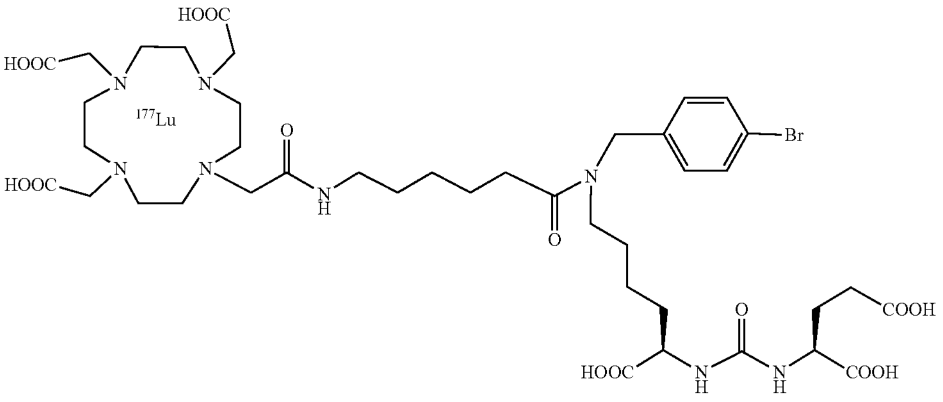
(IIId)
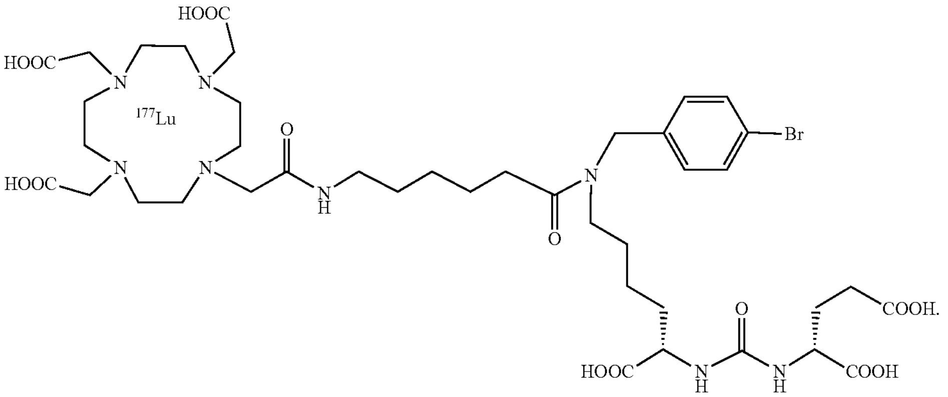
According to another embodiment, the compound of formula (I) is the compound of formula (IV):
(IV)
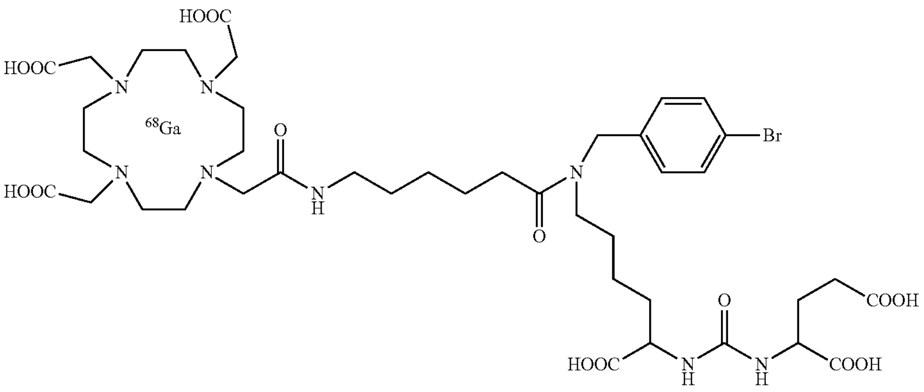
The compound of formula (IV) can be called $^{68}$Ga-PSMA-R2. Compounds of formula (IV) include the stereoisomers of formulae (IVa), (IVb), (IVc) and (IVd):

(IVa)
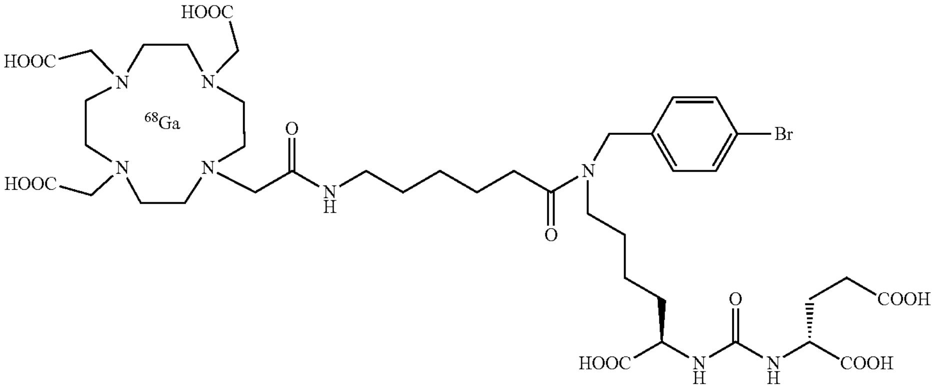
(IVb)
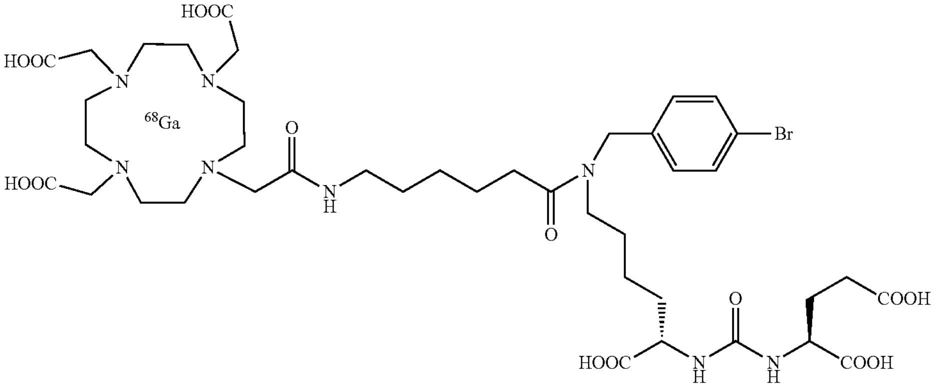
(IVc)
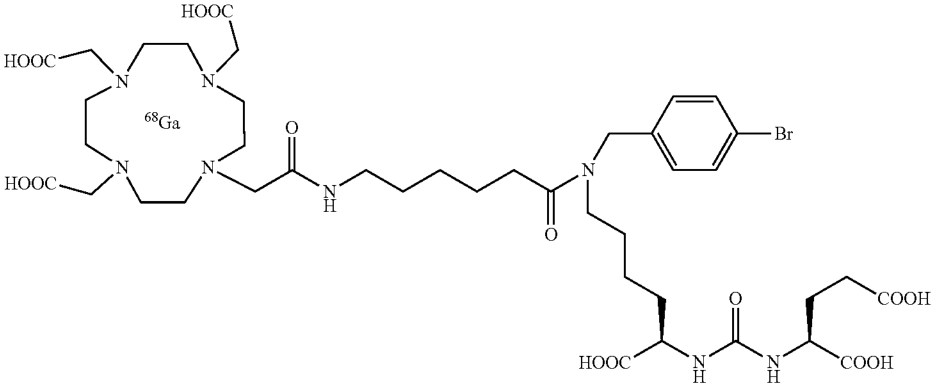
(IVd)
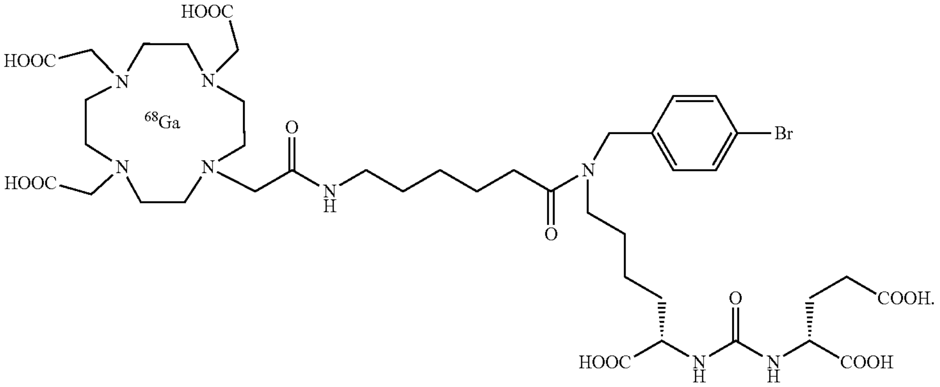

Pharmaceutical Composition

The disclosure also relates to a pharmaceutical composition comprising a compound of formula (I) to (IV) and at least one pharmaceutically acceptable carrier.

The form of the pharmaceutical compositions, the route of administration, the dosage and the regimen naturally depend upon the condition to be treated, the severity of the illness, the age, weight, and sex of the patient, etc.

The pharmaceutical compositions of the disclosure can be formulated for an intravenous, intramuscular or subcutaneous administration and the like.

The pharmaceutical compositions can take the form of an aqueous solution, for example an injectable formulation comprising at least one compound according this disclosure.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above.

For parenteral administration in an aqueous solution, for example, the solution may be suitably buffered and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In a particular, embodiment the pharmaceutical composition comprises one or more excipient(s) which is selected from stabilizers against radiolytic degradation, sequestering agents and mixtures thereof.

As used herein, "stabilizer against radiolytic degradation" refers to stabilizing agent which protects organic molecules against radiolytic degradation, e.g. when a gamma ray emitted from the radionuclide is cleaving a bond between the atoms of an organic molecules and radicals are forms, those radicals are then scavenged by the stabilizer which avoids the radicals undergo any other chemical reactions which might lead to undesired, potentially ineffective or even toxic molecules. Therefore, those stabilizers are also referred to as "free radical scavengers" or in short "radical scavengers". Other alternative terms for those stabilizers are "radiation stability enhancers", "radiolytic stabilizers", or simply "quenchers".

As used herein, "sequestering agent" refers to a chelating agent suitable to complex free radionuclide metal ions in the formulation (which are not complexed with the radiolabelled peptide).

The doses used for the administration can be adapted as a function of various parameters, and in particular as a function of the mode of administration used, of the relevant pathology, or alternatively of the desired duration of treatment. It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments described herein.

Compound of Formula (I) to (IV) for Use as a Medicament

The disclosure also relates to a compound of formula (I) to (IV) for use as a medicament. The compounds of formula (I) to (IV) exhibit valuable pharmaceutical properties as indicated in the tests provided in the examples and are therefore indicated for therapy.

The disclosure also relates to a compound of formula (I) to (IV) for use in treating cancer, in particular by targeted alpha therapy and by beta radiation.

Compound of formula (III) is particularly suitable for use as a medicament, preferably for use in treating cancer.

As used herein, the term "cancer" has its general meaning in the art and includes an abnormal state or condition characterized by rapidly proliferating cell growth. The term is meant to include all types of cancerous growths or oncogenic processes, metastatic tissues or malignantly transformed cells, tissues or organs, irrespective of histopathologic type or stage of invasiveness. The term cancer includes malignancies of the various organ systems, such as affecting skin, lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the oesophages.

Examples of cancer include, but are not limited, to hematological malignancies such as B-cell lymphoid neoplasm, T-cell lymphoid neoplasm, non-hodgkin lymphoma (NHL), B-NHL, T-NHL, chronic lymphocytic leukemia (CLL), small lymphocytic lymphoma (SLL), mantle cell lymphoma (MCL), NK-cell lymphoid neoplasm, and myeloid cell lineage neoplasm. Examples of non-hematological cancers include, but are not limited to, skin cancer, colon cancer, breast cancer, lung cancer, brain cancer, prostate cancer, head and neck cancer, pancreatic cancer, bladder cancer, colorectal cancer, bone cancer, cervical cancer, liver cancer, oral cancer, esophageal cancer, thyroid cancer, kidney cancer, stomach cancer and testicular cancer.

In a specific embodiment, the cancer is a cancer having PSMA expressing tumor or cells.

In a specific embodiment, the disclosure also relates to a compound of formula (I) to (IV) for use in a treating prostate cancer.

In a specific embodiment, the prostate cancer is a metastatic prostate cancer.

The disclosure also relates to a compound of formula (I) to (IV) for use in treating PSMA-expressing tumors or cells.

The PSMA-expressing tumor or cell can selected from the group consisting of: a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof. In some other embodiments, the PSMA-expressing tumors or cells is a prostate tumor or cell.

Hence, the disclosure also relates to a method for treating cancer, the method comprising contacting cancer cells with a therapeutically efficient amount of the compound of formula (I) to (IV).

As used herein, the term "contacting" means any action which results in at least one compound comprising the therapeutic agent of the presently disclosed subject matter physically contacting at least one cancer cell. Contacting can include exposing the cell(s) or tumor(s) to the compound in an amount sufficient to result in contact of at least one compound with at least one cell or tumor. The method can be practiced in vitro or ex vivo by introducing, and preferably mixing, the compound and cell(s) or tumor(s) in a controlled environment, such as a culture dish or tube. The method can be practiced in vivo, in which case contacting means exposing at least one cell or tumor in a subject to at least one compound of the presently disclosed subject matter, such as administering the compound to a subject via any suitable route.

In a specific embodiment, the cancer to treat is a cancer having PSMA expressing tumor or cells. For example, the cancer to treat can be a prostate cancer, which includes metastatic prostate cancer.

The disclosure also relates to a method for treating cancer, typically prostate cancer, the method comprising administering to a subject in need thereof, preferably a human, a therapeutically efficient amount of the compound of formula (I) to (IV).

As used herein, the term "treating" includes reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed compounds can be administered prophylactically to prevent or reduce the incidence or recurrence of the disease, disorder, or condition.

As used herein, the terms "therapeutically efficient amount" of a compound refer to an amount of the compound that will elicit the biological or medical response of a subject, for example, ameliorate the symptoms, alleviate conditions, slow or delay disease progression, or prevent a disease.

The disclosure also relates to a method for treating PSMA-expressing tumors or cells, the method comprising contacting PSMA-expressing tumors or cells with a therapeutically efficient amount of the compound of formula (I) to (IV).

The disclosure also relates to the use of a compound of formula (I) to (IV) for the manufacture of a medicament.

The disclosure also relates to the use of a compound of formula (I) to (IV) for the manufacture of a medicament for the treatment of cancer, like prostate cancer.

The disclosure also relates to the use of a compound of formula (I) to (IV) for the manufacture of a medicament for the treatment of PSMA-expressing tumors or cells.

Compound of Formula (I) to (IV) for Use in Imaging and Methods Thereof

The disclosure also relates to a compound of formula (I) to (IV) for use in imaging, preferably in vivo imaging.

The disclosure also relates to a compound of formula (I) to (IV) for use in imaging PSMA-expressing tumors or cells.

Compound of formula (IV) is particularly suitable for use in imaging, preferably for use in imaging PSMA-expressing tumors or cells.

In a specific embodiment, the imaging method in which the compound of formula (I) to (IV) is used is PET (positron emission tomography) or SPECT (Single photon emission computed tomography).

Hence, the disclosure also relates to a method for imaging, the method comprising contacting cancer cells with an effective amount of the compound of formula (I) to (IV).

The disclosure also relates to a method for imaging PSMA-expressing tumors or cells, the method comprising contacting PSMA-expressing tumors or cells with a therapeutically efficient amount of the compound of formula (I) to (IV). The method can further comprise a step of detecting the signal derived from the decay of the radiometal present in said compound.

The disclosure also relates to a method for imaging PSMA-expressing tumors or cells in a subject, the method comprising administering to said subject, preferably a human, a therapeutically efficient amount of the compound of formula (I) to (IV), and detecting the signal derived from the decay of the radiometal present in said compound.

In a specific embodiment, the present disclosure provides a method for detecting the presence or absence of PSMA-expressing tumors in a subject, comprising:

(i) administering a compound of formula (I) to (IV), e.g. as an intravenous injection in said subject;

(ii) acquiring an image, typically by PET or SPECT imaging; and, (iii) detecting the presence or absence of PSMA-expressing tumors in said subject.

The disclosure also relates to a compound of formula (I) to (IV) for use in diagnostic, typically for use in diagnosing cancer disorders, such as PSMA-expressing cancers.

The disclosure also relates to a method for diagnosing and/or detecting cancer cells or PSMA-expressing tumors or cells, for example prostate tumors or cells in a subject, the method comprising administering to said subject, preferably a human, a therapeutically efficient amount of the compound of formula (I) to (IV), and detecting the signal derived from the decay of the radiometal present in said compound.

Synthesis of the Compound of Formula (I) to (IV)

The compounds of formula (I) and (II) can be synthesized using the methods disclosed in WO2017/165473.

In particular, the compound of formula (II) can be synthesized as disclosed in scheme 1. The p-bromobenzyl group modified of Glu-Lys urea 2 can be prepared by reductive alkylation of Glu-Lys urea 1 with p-bromobenzaldehyde in presence of sodium cyanoborohydride in methanol. This procedure has been described in the literature (Tykvart et al. (2015) Journal of medicinal chemistry 58, 4357-63). Then, an aliphatic linker, Boc-6-aminohexanoic acid can be coupled on the same F-Lys amine of 2, for example using a base (like N,N-diisopropylethylamine) and a coupling agent (like N,N,N',N'-Tetramethyl-O-(N-succinimidyl)uronium tetrafluoroborate or 1-[Bis(dimethylamino)methylene]-1H-1,2,3-triazolo[4,5-b]pyridinium 3-oxid hexafluorophosphate), to yield compound 3. Compound 3 can then be deprotected to yield compound 4, for example using an acid like trifluoroacetic acid. Finally, conjugation with commercially available DOTA-NHS ester can be performed to yield compound (II).

The compounds of formula (I) and (II) can be radiolabeled using methods which are commonly used in the field of radiolabeling. In particular, the compound of formula (II) can also be radiolabeled with $^{177}$Lu, to form the compound of formula (III), using the method described in WO2017/165473. The compound of formula (II) can also be radiolabeled with $^{68}$Ga, to form the compound of formula (IV), using the method described in WO024013.

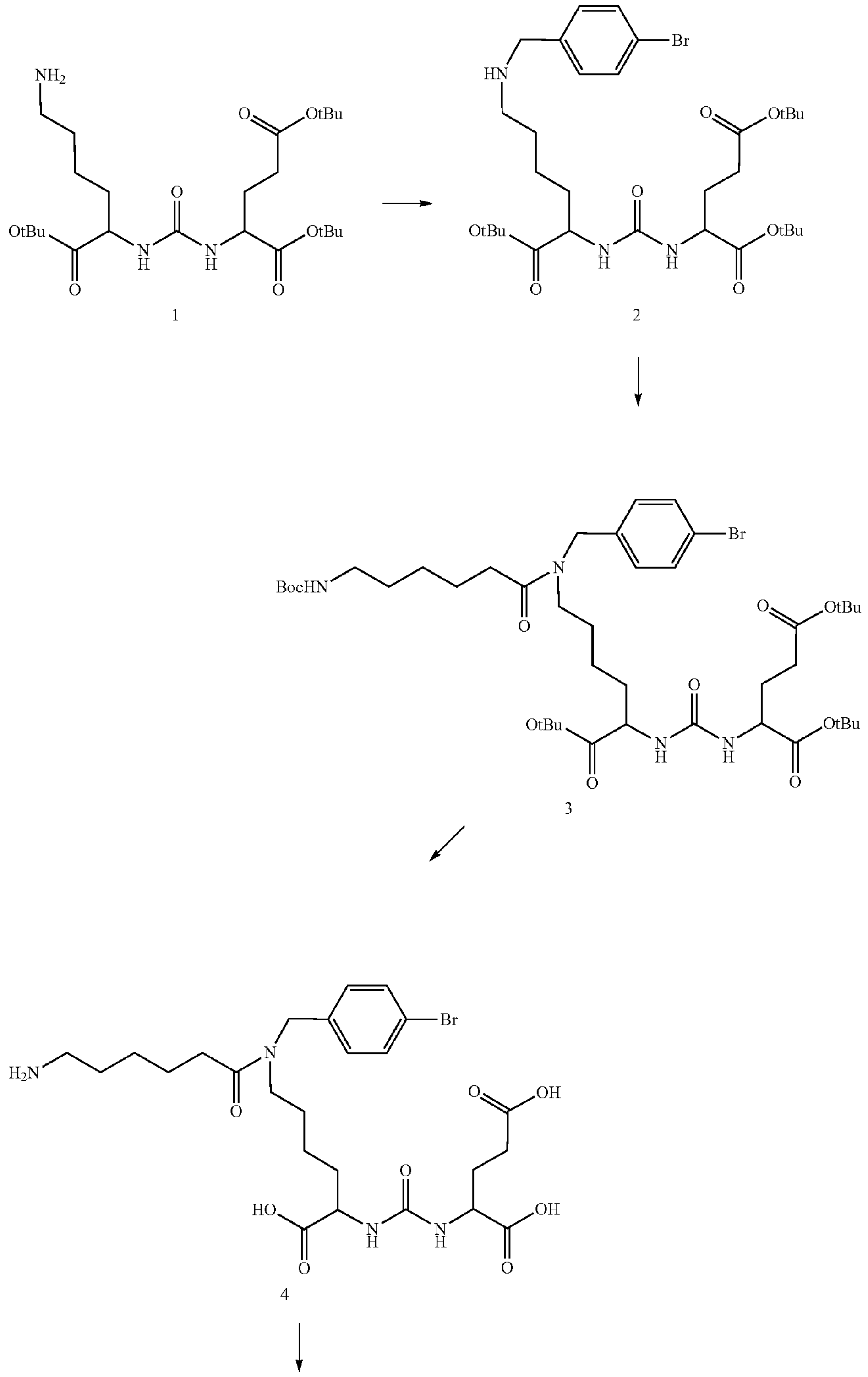

1

2

3

4

-continued

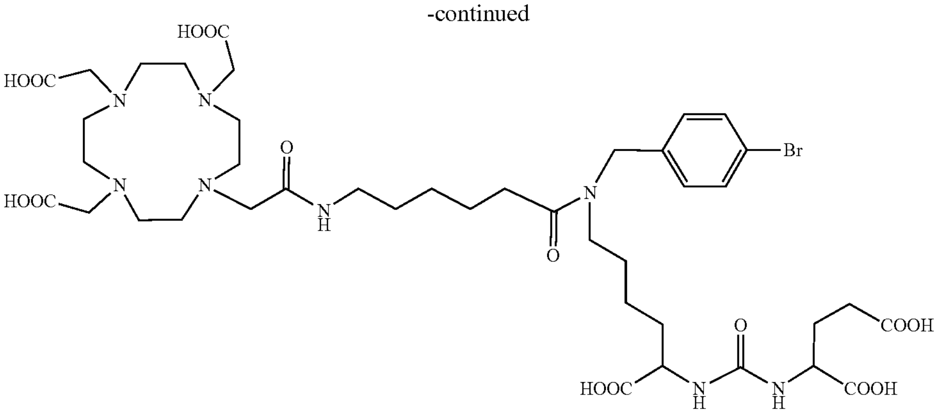

(II)

EXAMPLES

Example 1: In Vivo Distribution in Healthy Animals (Study Performed with $^{68}$Ga-PSMA-R2)

In vivo distribution studies were performed in CD-1 healthy mice using Ga-labelled PSMA-R2, which was administered intravenously at a dose of 120-150 μCi (4.44-5.55 MBq). At specific time points after intravenous injection, animals (3 or 4/group) were sacrificed, organs collected, weighted and evaluated in a gamma counter. The calculated % ID/g values are reported in FIG. 1 and FIG. 2.

Figure 2:
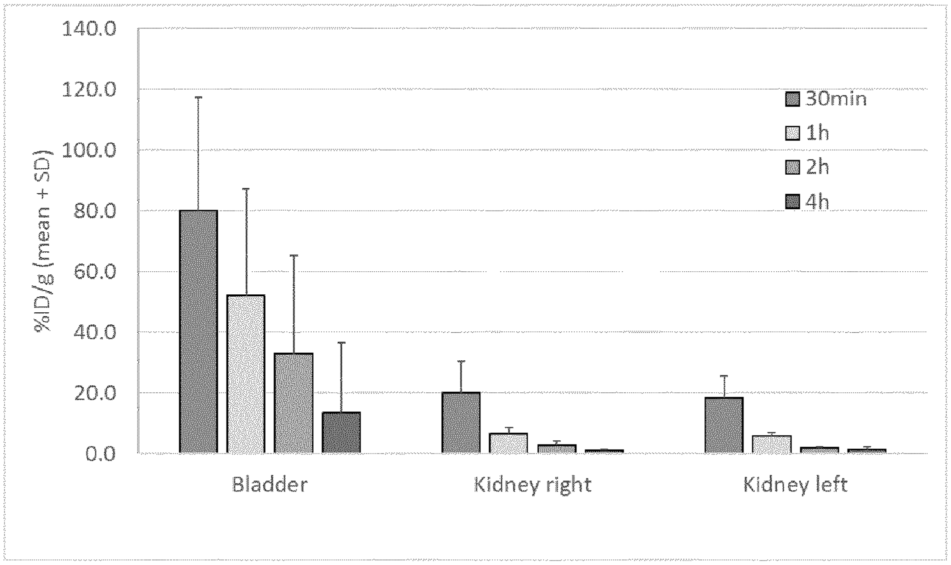
FIG. 2 shows the $^{68}$Ga-PSMA-R2 biodistribution in healthy CD-1 mice (bladder and kidney) (Mean±SD) according to example 1.

$^{68}$Ga-PSMA-R2 uptake in kidneys and bladder indicated that the radiotracer was excreted through the renal system (FIG. 2). Liver uptake recorded was very low (0.74% at 30 minutes decreasing to 0.21% at 4 hours), indicating minimum excretion through the hepatobiliary system (FIG. 1). Although slightly high radiotracer uptake was recorded in blood and other organs such as adrenals, lungs, thyroid at the earliest time-point (30 min), the % ID value decreased rapidly at the later time points (FIG. 1). Low radiotracer uptake was detected in the remaining organs (intestine, pancreas, muscle, bone) at all time-points (including the earliest one, 30 min).

Example 2: In Vivo Distribution in Tumor Models (Study Performed with $^{68}$Ga-PSMA-R2)

Figure 3:
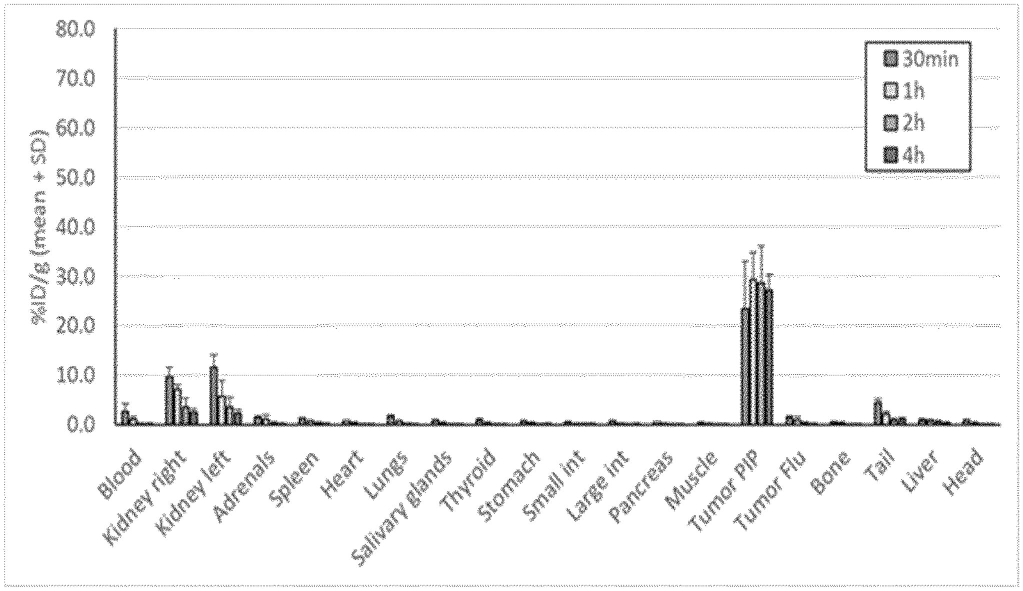
FIG. 3 shows the $^{68}$Ga-PSMA-R2 biodistribution (Mean±SD) in athymic nude mice bearing PSMA positive tumor (PIP) and negative (Flu) according to example 2.

Athymic nude male mice bearing the PC-3 PSMA positive and PSMA negative tumor xenografts were injected with approximately 4.5 MBq of $^{68}$Ga-PSMA-R2, and subsequently assessed for biodistribution and imaging studies. At 4 time points (30 min, 1 h, 2 h and 4 h) post injection (p.i.), tumor and organ uptake was determined using a gamma-counter. To assess receptor-specificity additional groups of animals were coinjected with an excess of unlabeled PSMA-R2 (40 nmol). The results are shown in FIG. 3.

The same study was performed with $^{68}$Ga-PSMA-cpd 2, a comparative compound of the following formula:

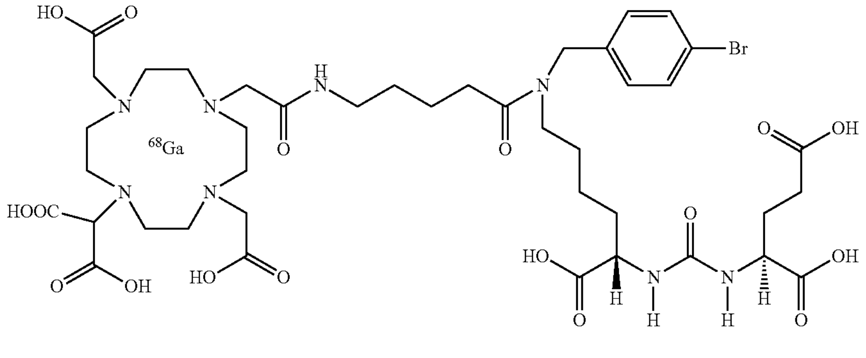

Figure 4:
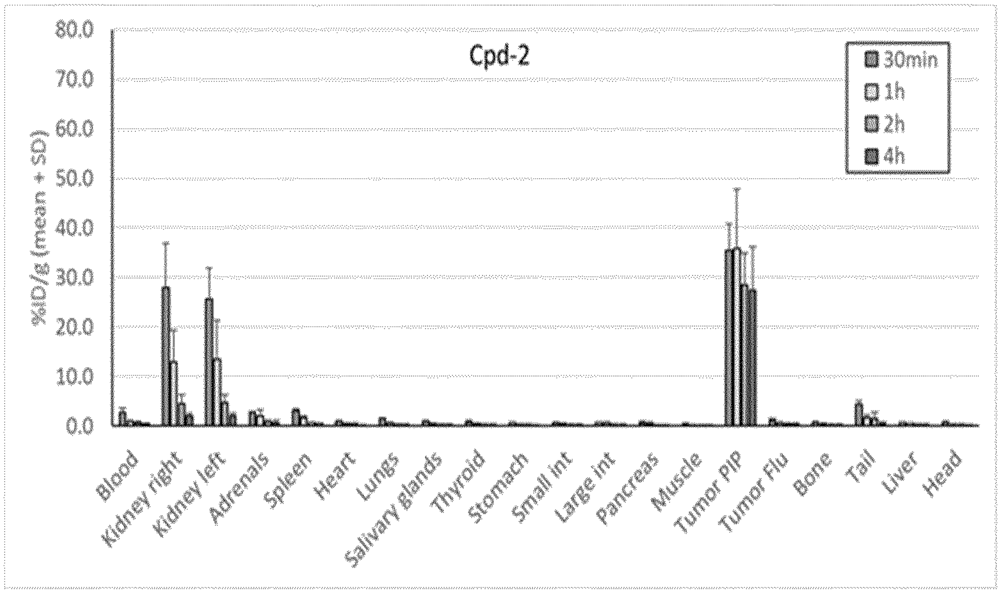
FIG. 4 shows the $^{68}$Ga-PSMA-cpd 2 biodistribution (Mean±SD) in athymic nude mice bearing PSMA positive tumor (PIP) and negative (Flu) according to example 2.

The results are shown in FIG. 4.

The tumor uptake, kidney uptake, salivary glands uptake and the tumor-to-kidney ratio for $^{68}$Ga-PSMA-R2 and $^{68}$Ga-PSMA-cpd 2 are summarized in table 1.

TABLE 1

Comparison of $^{68}$Ga-PSMA-R2 and $^{68}$Ga-PSMA-cpd 2

| | $^{68}$Ga-PSMA-R2 | $^{68}$Ga-PSMA-cpd2 |
|---|---|---|
| Tumor uptake | 29% (1 h) | 36% (1 h) |
| Kidney uptake | 6% (1 h) | 13% (1 h) |
| Tumor-to-kidney ratio | 5 (1 h) | 3 (1 h) |
| Salivary glands | 0.81% (0.5 h) | 0.95% (0.5 h) |

These results show that, after 1 hour, the kidney uptake and the salivary gland uptake are lower for $^{68}$Ga-PSMA-R2 compared to comparative compound $^{68}$Ga-PSMA-cpd2.

Moreover, the tumor-to-kidney ratio is higher in the case of $^{68}$Ga-PSMA-R2.

This indicates a possible lower toxicity of $^{68}$Ga-PSMA-R2 compared to $^{68}$Ga-PSMA-cpd2. Furthermore, the high tumor-to-kidney ratio after 1 hour suggest a better visualization of the tumor in the case of $^{68}$Ga-PSMA-R2, as the optimal imaging timepoint is 45 minutes to 1 hour.

Example 3: In Vivo Efficacy on Mice in PC3-PIP PSMA Positive Model

An efficacy study was conducted in a prostate cancer model using Lu-labelled PSMA-R2).

Mice bearing PC3-PIP (PSMA positive) tumor were injected once with 111MBq of $^{177}$Lu-PSMA-R2, $^{177}$Lu-PSMA-617, included as reference compound, or with saline (control).

Tumor volume is expressed either as an absolute value ($mm^3$) or relatively to the volume measured at the time of the first injection.

Figure 5:
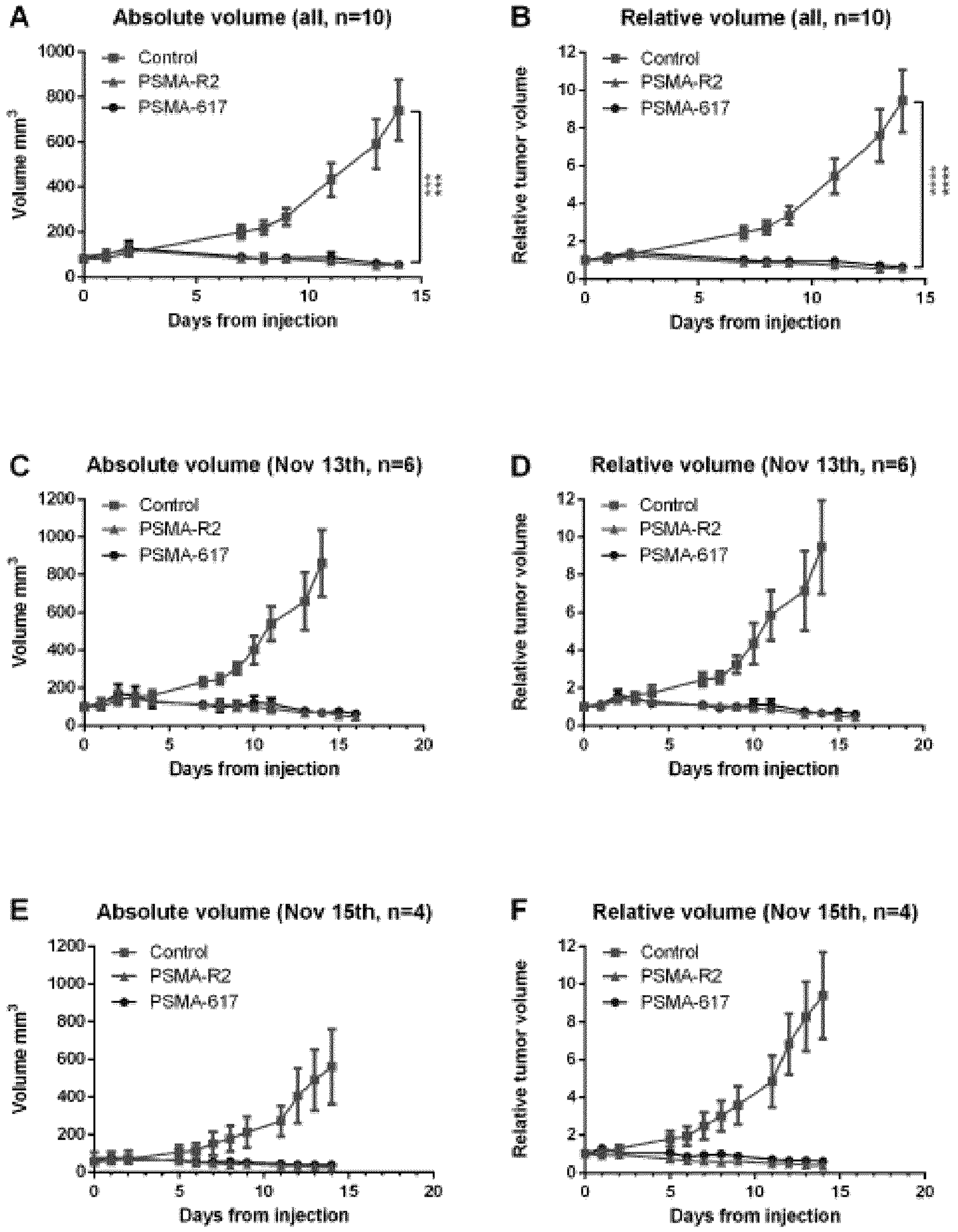
FIG. 5 shows $^{177}$Lu-PSMA-R2 and $^{177}$Lu-PSMA-617 efficacy study in athymic nude mice bearing tumor PSMA positive (PIP) according to example 3.

The results of absolute tumor volumes show that tumor volume are significantly reduced in the $^{177}$Lu-PSMA-R2 and $^{177}$Lu-PSMA-617 groups in comparison to control group ($p<0.001$) (cf. FIG. 5A).

Similarly, when data are expressed as relative volumes, tumor volumes from both $^{177}$LuPSMA-R2 and $^{177}$Lu-PSMA-617 groups are found to be significantly reduced in comparison to control group ($p<0.001$) (cf. FIG. 5B).

No differences were observed between the two treated groups tumor volumes either when expressed as absolute or relative volume. In FIG. 5C-F, absolute tumor volume and relative tumor volume of the two subgroups treated at an interval of two days are shown.

These results show that $^{177}$Lu-PSMA-R2 is effective in reducing the tumor sizes of PSMA positive tumors in mice. $^{177}$Lu-PSMA-R2 thus exhibit valuable pharmaceutical properties and can therefore be indicated for therapy.

Example 4: Safety Pharmacology

Behavioral Irwin Tests and Effect on Body Temperature Following Single Intravenous Administration in the Rat The aim of this study was to evaluate the possible effects of $^{175}$Lu-PSMA-R2, at doses of 0.2, 0.6 and 2.0 mg/kg, on general behavior parameters in the rat after intravenous administration, according to the study design in Table 2.

TABLE 2

Experimental design of the behavioral Irwin test

| Group Number | Treatment (mg/kg) + | Dose level | Dose volume (ml/kg) | Number of rats and gender |
|---|---|---|---|---|
| 1 | 0 | Vehicle | 5 | 5M |
| 2 | 0.2 | Low | 5 | 5M |
| 3 | 0.6 | Medium | 5 | 5M |
| 4 | 2.0 | High | 5 | 5M |

+: in terms of test item as supplied.

The following parameters were evaluated: mortality, body weight, clinical signs and Irwin test.

The Irwin test was performed at the following intervals after dosing: 5, 15, 30 minutes and 1, 2 and 24 hours.

A single intravenous administration of $^{175}$Lu-PSMA-R2, at doses of 0.2, 0.6 and 2.0 mg/kg, did not induce any effects on behavioral, neurologic or autonomic parameters in the Irwin study in rats up to 24 h post-dose. No deaths occurred during the study and no clinical signs were observed during the 6-day observation period.

The results of the study are summarized in Table 10.

Evaluation of Effect on Respiration in the Unrestrained Conscious Rat Following Single Intravenous Administration The aim of this study was to assess the possible effects of 0.2, 0.6 and 2.0 mg/kg $^{175}$LuPSMA-R2 on respiratory function of conscious rats via a whole-body plethysmography method after intravenous administration according to the study design detailed in Table 3.

TABLE 3

Experimental design of the study on the evaluation of the effects on respiratory function

| Group Number | Treatment (mg/kg) | Dose level | Dose volume (mL/kg) | Theophylline (mg/kg) | Number of rats and gender |
|---|---|---|---|---|---|
| 1 | 0 | Vehicle | 5 | 0 | 8M |
| 2 | 0.2 | Low | 5 | 0 | 8M |
| 3 | 0.6 | Mid | 5 | 0 | 8M |
| 4 | 2.0 | High | 5 | 0 | 8M |
| 5 | 0 | Reference | 5 | 25 | 8M |

Inspiratory time, expiratory time, peak inspiratory flow, peak expiratory flow, tidal volume, relaxation time, minute volume, respiratory rate and enhanced pause were continuously recorded from approximately 1 hour before dosing up to 4 hours after dosing. Respiratory Number of rats and gender parameters were reported pre-dose and at 5, 15 and 30 minutes and 1, 1.5, 2, 3 and 4 hours after dosing. Clinical signs were recorded on the day of dosing.

The results of the study are summarized in Table 10.

Effects on the Cardiovascular Function of the Conscious Minipig Following Intravenous Administration The purpose of this study was to investigate the potential effects of $^{175}$Lu-PSMA-R2 on the cardiovascular functions of the conscious telemetered male minipig following intravenous administration at doses of 0.058, 0.175 and 0.583 mg/kg. The experimental design is shown in Table 4.

The test item or vehicle was administered intravenously into the external auricular vein at a fixed injection rate of 4 mL/min. The dose was administered to each animal at a dose volume of 1 mL/kg body weight.

At 7-day intervals, each animal received the vehicle or one of the three doses of the test item, following the crossover design described in Table 4.

TABLE 4

Experimental design of the study on the evaluation of the effects on the cardiovascular function in male minipigs

| Animal Number | Treatment: $^{175}$Lu-PSMA-R2 (mg/kg) 1$^{st}$ Day 1 | 2$^{nd}$ Day 8 | 3$^{rd}$ Day 15 | 4$^{th}$ Day 22 |
|---|---|---|---|---|
| 2 | Vehicle | 0.058 | 0.175 | 0.583 |
| 4 | 0.058 | 0.175 | 0.583 | Vehicle |
| 6 | 0.175 | 0.583 | Vehicle | 0.058 |
| 8 | 0.583 | Vehicle | 0.058 | 0.175 |

Systolic, diastolic and mean blood pressure (SBP, DBP and MBP), heart rate (HR), body temperature and Lead II electrocardiogram were recorded continuously, from 1 hour before administration up to 24 h after dosing. Haemodynamic and electrocardiographic data were reported at pre-dose and at 5, 15, 30 minutes and 1, 2, 4, 8 and 24 hours post-dose.

The results of the study are summarized in Table 10.

Single and Repeated Dose Toxicity Studies

Single and repeated dose toxicity studies have been performed with a Lu-PSMA-R2 solution. The preclinical toxicity studies were conducted on $^{175}$Lu-PSMA-R2 as surrogate of the $^{177}$Lu-PSMA-R2.

The test item $^{175}$Lu-PSMA-R2 is a solution containing $^{175}$Lu-PSMA-R2 and unlabeled PSMA-R2, in acetate buffer, in which PSMA-R2 is at a nominal concentration of 1 mg/mL and it is present partly in the free form (PSMA-R2) and partly complexed with Lu-175, the ratio between the two being around 1:1. The dose is expressed as the sum of the free and 175 Lu-labelled form.

Single dose toxicity studies in rats and minipigs have been concluded as well as the 2-week repeated dose toxicity studies in rats.

Single Dose Toxicity Study in the Rat

This study aimed at assessing the toxicity of $^{175}$Lu-PSMA-R2 right after acute intravenous injection of 2 or 4 mg/kg among Sprague Dawley (SD) rats.

Two groups of 30 animals (1:1 male:female ratio) were administered with 2 and 4 mg/kg, respectively. A control group of equal characteristics was treated with the vehicle (Table 5).

TABLE 5

Experimental design of the single dose toxicity study in the rat

| Group Number | Treatment dose (mg/kg) | Dose level | Injection volume (mL/kg) | Number of rats and gender |
|---|---|---|---|---|
| 1 | 0 | Control | 5 | 15M + 15F |
| 2 | 2 | First | 5 | 15M + 15F |
| 3 | 4 | Second | 5 | 15M + 15F |

Signs of reaction to treatment at all doses were assessed at 30, 120 and 240 min p.i. as well as 24 h later. At Day 2, 10 rats per gender and per group were sacrificed. The remaining 5 animals/gender/group were observed daily over 14 days.

Body weight was recorded on the day of treatment group allocation, Day 1 (day of injection), 8 and 15. Food consumption was measured on Day 2 and weekly thereafter. At the end of treatment, urine samples were collected for urinalysis. On Day 2 and 15, blood samples withdrawn at sacrifice were screened for clinical pathologies. After dissection, organs were weighted and tissues were treated for microscopic analyses (over 50 different tissues were analyzed).

The results of the study are summarized in Table 10. They suggest that a single intravenous administration of the test item, $^{175}$Lu-PSMA-R2, at dose levels of 2 and 4 mg/kg (that is about 480 and 960 times the intended human dose, scaled based on mg/kg, considering a human body weight of 60 kg), did not induce toxicity signs and is therefore well tolerated in rats.

Single Dose Toxicity Study in the Minipig

The toxicity and the toxicokinetic profile of $^{175}$Lu-PSMA-R2 were investigated in Gottingen minipigs after single bolus intravenous administration according to the experimental design detailed in Table 6.

A two-week treatment-free period was allowed after administration.

All animals were administrated intravenously. Plasma samples were collected at Day 1 for toxicokinetic analysis.

TABLE 6

Experimental design of the single dose toxicity study in the minipig

| Group Number | Treatment dose (mg/kg) | Dose level | Injection volume (mL/kg) | Number of minipigs and gender |
|---|---|---|---|---|
| 1 | 0 | Control | 2.5 | 3M + 3F |
| 2 | 0.175 | First | 2.5 | 3M + 3F |
| 3 | 0.583 | Second | 2.5 | 3M + 3F |
| 4 | 1.750 | Third | 2.5 | 3M + 3F |

Mortality, clinical signs, body weight, food consumption, clinical pathology investigations, ophthalmoscopy, ECG evaluations, and macroscopic observations were indexed at necropsy. Then selected organs were weighed and tissues collected.

In addition, plasma samples were collected on Day 1 for toxicokinetic analysis.

The results of the study are summarized in Table 10. They suggest that a single intravenous administration of the test item, $^{175}$Lu-PSMA-R2, at dose levels of 0.175, 0.583 and 1.75 4 mg/kg (that is about 42, 140 and 420 times the intended human dose, scaled on a mg/kg basis, considering a body weight of 60 kg), did not induce signs of toxicity to the minipigs. Therefore, it can be concluded that the test item is well tolerated by the minipigs at these amounts.

Repeated Dose Toxicity Study in the Rat

The purpose of this study was to investigate the toxicity of $^{175}$Lu-PSMA-R2 in rats after daily intravenous administration for 2 weeks and recovery from any treatment related effects during a 2-week recovery period (main groups).

The tested doses were 0.13, 0.39 and 1.29 mg/kg/day, that is about 31, 93 and 310 times the PSMA-R2 anticipated human dose.

Each main treatment group consisted of 10 male and 10 female rats. There were additional 5 male and 5 females included to be sacrificed after 2 weeks of recovery in groups 1 and 4. Two satellite groups (low and mid-dose) for toxicokinetics had 9 male and 9 female animals and one group (high dose) included 12 male and 12 female animals. One additional group (control) comprised 3 male and 3 female animals.

The experimental design is schematized in Table 7 and Table 8.

TABLE 7

Experimental design of the repeated dose toxicity study in the rat - main groups.

| Group Number | Treatment dose (mg/kg/day) | Dose level | Injection volume (mL/kg) | Number of rats and gender: Main phase | Number of rats and gender: Recovery phasc |
|---|---|---|---|---|---|
| 1 | 0 | Control | 2.5 | 10M + 10F | 5M + 5F |
| 2 | 0.13 | Low | 2.5 | 10M + 10F | |
| 3 | 0.39 | Medium | 2.5 | 10M + 10F | |
| 4 | 1.29 | High | 2.5 | 10M + 10F | 5M + 5F |

TABLE 8

| Experimental design of the repeated dose toxicity study in the rat - satellite groups for TK evaluation | | | | |
|---|---|---|---|---|
| Group Number | Treatment dose (mg/kg/day) | Dose level | Injection volume (mL/kg) | Number of rats and gender |
| 5 | 0 | Control | 2.5 | 3M + 3F |
| 6 | 0.33 | Low | 2.5 | 9M + 9F |
| 7 | 0.39 | Medium | 2.5 | 9M + 9F |
| 8 | 1.29 | High | 2.5 | 12M + 12F |

In this study, the toxicity and the toxicokinetic profile of $^{175}$Lu-PSMA-R2 were investigated in Sprague Dawley rats after daily intravenous administration for 2 weeks at the dosages of 0.13, 0.39 and 1.29 mg/kg/day. A 2-week treatment-free period, for the control and high dose groups, was allowed to recover from any treatment-related effects or persistence of adverse effects observed during the 2-week dosing phase.

No signs of toxicological significance were recorded at daily clinical observation. Bodyweight and food consumption were unaffected by treatment. No anomalies related to treatment were observed at ophthalmoscopy examination. No findings of toxicological relevance were found at clinical pathology examination. No evidence of treatment-related effects was found at necropsy, organ weights or histopathological examination.

The toxicokinetic evaluation showed that all animals treated at the three dose levels were exposed to the test item. In general, the exposure was approximately dose proportional. The exposure was similar in males and females. The drug was eliminated with a half-life of approximately 0.4-0.8 hours considering both sexes and all dose levels. The clearance was dose-independent suggesting a linear kinetic behaviour. No accumulation was observed after daily administration, from Day 1 to Day 14.

On the basis of the results obtained in this study, no toxic effects were seen in treated mixed groups when compared to controls. Therefore 1.29 mg/kg/day can be considered as the NOAEL (No Observed Adverse Effect Level), which is which is 310 times higher than the foreseen human dose.

The results of the study are summarized in Table 10.

Repeated Dose Toxicity Study in the Minipig

The purpose of this study is to investigate the toxicity and the toxicokinetic profile of LuPSMA-R2 in minipigs after daily intravenous administration for 2 weeks and recovery from any treatment-related effects during a recovery period of 2 weeks.

The tested doses are: 0.058, 0.175 and 0.583 mg/kg/day, that is about 14, 42 and 140 times the PSMA-R2 anticipated human dose.

Each group included 3 male and 3 female minipigs. Groups 1 and 4 included 2 additional animals per gender to be sacrificed after 2 weeks of recovery. The experimental design is summarized in Table 9.

All animals were dosed intravenously once a day for 14 consecutive days.

TABLE 9

| Experimental design of the repeated dose toxicity study in the minipig | | | | | |
|---|---|---|---|---|---|
| | Treatment | | Injection | Number of minipigs and gender | |
| Group Number | dose (mg/kg/day) | Dose level | volume (mL/kg) | Main phase | Recovery phase |
| 1 | 0 | Control | 1 | 3M + 3F | 2M + 2F |
| 2 | 0.058 | Low | 1 | 3M + 3F | |
| 3 | 0.175 | Medium | 1 | 3M + 3F | |
| 4 | 0.583 | High | 1 | 3M + 3F | 2M + 2F |

Body weights and food intake were unaffected by the treatment. Physical examination performed did not show appreciable changes in any animal. No treatment-related abnormalities were detected at ophthalmoscopy and at the electrocardiographic examination. Clinical pathology (i.e.: haematology, coagulation, blood chemistry and urine analysis), as well as gross pathology, terminal body weight and absolute and relative organ weight did not reveal notable or treatment-related changes at any dose, with no histopathology treatment-related modifications.

The toxicokinetic evaluation showed that all animals treated at the three dose levels were exposed to the test item. On Day 1 the estimated $^{175}$Lu-PSMA-R2 half-life was 0.71 and 0.63 hour, in male and female minipigs, respectively, considering the mean value per sex. These values were confirmed on Day 14. The plasma clearance was dose-independent, suggesting a linear kinetic behaviour. The increase in systemic exposure (in terms of Cmax and AUC0–tlast) was approximately dose-proportional. No relevant accumulation after daily administration was observed from Day 1 to Day 14.

The results of this study indicate that 0.583 mg/kg/day can be considered as the NOAEL for this study.

The results of the safety pharmacology and toxicology studies are summarized in Table 10.

TABLE 10

| Summary of the results obtained in the safety pharmacology and toxicology studies | | |
|---|---|---|
| Study | Doses (mg/kg) [times the human dose] | Status/Results |
| Safety pharmacology: effects on CNS in rats (Irwin test) | 0.2, 0.6, 2 mg/kg [48x, 144x, 480x] | No effects on behavioural, neurologic or autonomic parameters up to 24 h post-dose. No deaths occurred during the study. No clinical signs were observed at the 6 day obs period. |
| Safety pharmacology: effects on respiratory function in rats | 0.2, 0.6, 2 mg/kg [48x, 144x, 480x] | No changes of toxicological significance were observed in respiratory parameters recorded over 4 hours post-injection. |

TABLE 10-continued

| Summary of the results obtained in the safety pharmacology and toxicology studies | | |
|---|---|---|
| Study | Doses (mg/kg) [times the human dose] | Status/Results |
| Evaluation of effect on blood pressure, heart rate, electrocardiogram and body temperature in mini-pigs | 0.058, 0.175, 0.58 mg/kg [14x, 42x, 140x] | No relevant changes in heart rate, arterial blood pressure or electrocardiogra were observed at the tested doses in conscious minipigs. |
| Extended single dose toxicity in rats | 2, 4 mg/kg [480x, 960x] | No signs of toxicity observed. One death at 30 min after dosing (high dose). No cause of death could be established after histopath examination. Only decreased activity was noted in this animal (and in 5 other animals of the high dose group) immediately after dosing. Conclusion: of the test item, 175Lu-PSMA-R2 did not induce toxicity signs after single iv admin, therefore is well tolerated in rats. |
| Single dose toxicity in minipigs | 0.175, 0.58, 1.75 mg/kg [42x, 140x, 420x] | No relevant treatment-related toxicity signs, compound well tolerated in mini pigs at the doses tested. No treatment-related physical signs, ocular findings, nor electrocardiogramabnormalities. Some changes in hematology and clinical chemistry were observed in some animals of the high dose group No changes in the organ weights and no treatment-related macroscopic or microscopic changes were observed. |
| Repeated dose (2 weeks) toxicity in rats | 0.13, 0.39, 1.29 mg/kg [31x, 93x, 310x 1 | No evidence of treatment-related effects were found in treated groups when compared to controls. Therefore 1.29 mg/kg/day could be stated as the NOAEL (No Observed Adverse Effect Level). |
| Repeated dose (2 weeks) toxicity in minipigs | 0.058, 0.175, 0.58 mg/kg [14x, 42x, 10x] | The compound was well tolerated in mini pigs when administered once a day for 2 weeks consecutively. No evidence of treatment-related effects were found in treated groups when compared to controls. Therefore 0.58 mg/kg/day could be stated as the NOAEL (No Observed Adverse Effect Level). |

Genotoxicity Studies: Bacterial Mutation Assay

The test item $^{175}$Lu-labelled PSMA-R2 solution was examined for the ability to induce gene mutations in tester strains of *Salmonella typhimurium* and *Escherichia coli*, as measured by reversion of auxotrophic strains to prototrophy. The five tester strains TA1535, TA1537, TA98, TA100 and WP2 uvrA were used. Experiments were performed both in the absence and presence of metabolic activation, using liver S9 fraction from rats pre-treated with phenobarbital and 5,6-benzoflavone.

The test item was used as a solution in sodium acetate buffer and all concentrations in this report are expressed in terms of active ingredient. The test item $^{175}$Lu-labelled PSMA-R$^2$ solution was assayed in the toxicity test at a maximum feasible concentration of 1000 pg/plate and at four lower concentrations spaced at approximately half-log intervals: 316, 100, 31.6 and 10.0 μg/plate. No precipitation of the test item was observed at the end of the incubation period at any concentration. Neither toxicity, nor relevant increases in revertant numbers were observed with any tester strain at any dose level, in the absence or presence of S9 metabolism.

On the basis of the results obtained in the preliminary toxicity test, in the Main Assay, using the plate incorporation method, the test item was assayed with all tester strains at the following dose levels: 1000, 500, 250, 125 and 62.5 μg/plate. No precipitation of the test item was observed at the end of the incubation period at any concentration. Neither toxicity, nor relevant increases in revertant numbers were observed with any tester strain at any dose level, in the absence or presence of S9 metabolism. Since a clear negative result was obtained, no further experiment was undertaken.

It is concluded that the test item $^{175}$Lu-labelled PSMA-R2 solution does not induce reverse mutation in *Salmonella typhimurium* or *Escherichia coli* in the absence or presence of S9 metabolism, under the reported experimental conditions.

In Vitro Stability in Plasma

Stability of PSMA-R2 ligand was assessed in vitro after incubation with plasma from four different species (mouse, rat, mini-pig and human). PSMA-R2 was incubated at 37° C. in the different matrices, at a final concentration of 10 μg/mL, for 30, 60 and 120 minutes. The samples were analyzed by LC-MS/MS method.

PSMA-R2 showed good stability in human plasma, with 85% recovery after 2 hours.

Plasma Protein Binding Studies

Plasma protein binding of PSMA-R2 and $^{175}$Lu-PSMA-R2 has been determined by ultrafiltration method, after incubation of the compounds in human, mouse, rat and minipig plasma at two different concentrations: 1 and 5 μg/mL. The results (as percentage of fraction unbound) are reported in Table 11.

TABLE 11

PSMA-R2 plasma protein binding results expressed as percentage of fraction unbound

| Species | PSMA-R2 fu (%) | | 175Lu-PSMA-R2 fu (%) | |
|---|---|---|---|---|
| 5 µg/ml | 1 µg/mL | 5 µg/mL | 1 µg/mL | |
| Human | 23.0 ± 0.5 | 29.9 ± 4.6 | 45.0 ± 9.6 | 43.9 ± 5.1 |
| Mouse | 72.7 ± 1.5 | 86.2 ± 11.1 | 71.0 ± 2.2 | 71.1 ± 44 |
| Rat | 22.6 ± 1.1 | 25.6 ± 1.8 | 50.8 ± 4.4 | 37.4 ± 4.9 |
| Minipig | 35.3 ± 8.5 | 40.7 ± 4.3 | 46.3 ± 12.5 | 41.1 ± 4.2 |

The results support that $^{175}$Lu-PSMA-R2 is a non-highly bound compound, the unbound fraction of the $^{175}$Lu-labelled or unlabelled PSMA-R2 in human plasma ranging from about 25% to 45%. The results of protein binding rat plasma and minipig plasma are in the same range. The mouse showed a lower protein binding compared to the other species, the unbound fraction ranging from about 70% to 86%. In general, in all species, the results at the two different concentrations tested are quite similar.

That which is claimed:

1. A compound of formula (1):

(1)

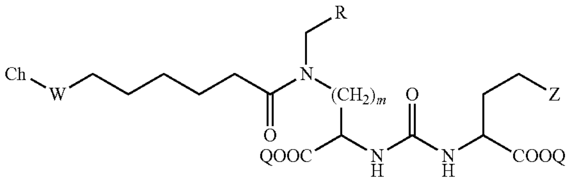

wherein:

Z is COOQ;

Q is H;

m is 4;

R is

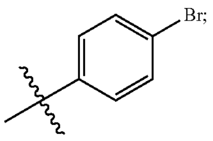 [SMILES: *c1ccc(Br)cc1]

W is —(C═O)—$NR^2$;

$R^2$ is H;

Ch is a chelating agent having a structure of

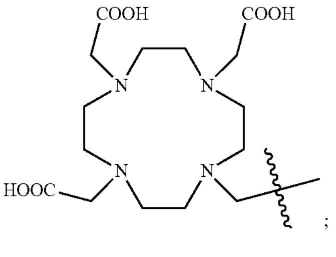 [SMILES: *CN1CCN(CC(=O)O)CCN(CC(=O)O)CCN(CC(=O)O)CC1]

optionally comprising a metal or a radiometal; and pharmaceutically acceptable salts thereof.

2. The compound of formula (I) according to claim 1, wherein the compound is a compound of formula (Ia), (Ib), (Ic) or (Id):

(Ia)

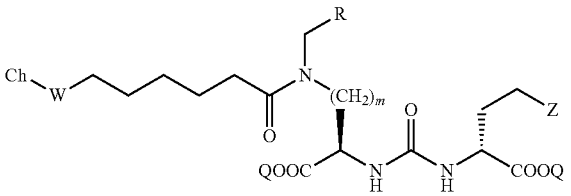

(Ib)

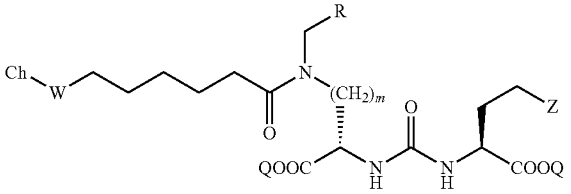

(Ic)

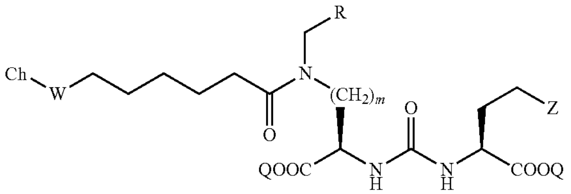

(Id)

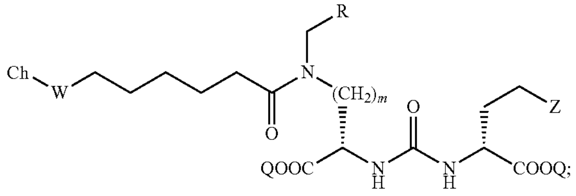

wherein:

Z is COOQ;

Q is H;

m is 4;

R is

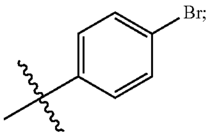 [SMILES: *c1ccc(Br)cc1]

W is —(C═O)—$NR^2$;

$R^2$ is H;

Ch is a chelating agent having the structure:

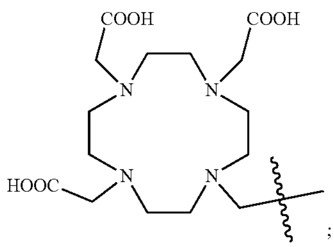 [SMILES: *CN1CCN(CC(=O)O)CCN(CC(=O)O)CCN(CC(=O)O)CC1]

;

optionally comprising a metal or a radiometal; and pharmaceutically acceptable salts thereof.

3. The compound of formula (I) according to claim 1, wherein Ch comprises a metal selected from Y, Lu, Tc, Zr, In, Sm, Re, Cu, Pb, Ac, Bi, Al, Ga, Re, Ho and Sc.

4. The compound of formula (I) according to claim 3, wherein the metal is a radiometal selected from $^{68}$Ga, $^{64}$Cu, $^{86}$Y, $^{90}$Y, $^{89}$Zr, $^{111}$In, $^{99m}$Tc, $^{177}$Lu, $^{153}$Sm, $^{186}$Re, $^{188}$Re, $^{67}$Cu, $^{212}$Pb $^{22}$Ac, $^{213}$Bi, $^{212}$Bi, $^{212}$Pb, $^{67}$Ga, $^{203}$Pb, $^{47}$Sc, and $^{166}$Ho.

5. The compound of formula (I) according to claim 1, wherein the compound is distributed in the body of a tumor bearing animal or human in such a way that, 1 h after the intravenous injection of the compound, the tumor-to-kidney ratio is at least 5.

6. The compound of formula (I) according to claim 1, wherein the compound is a compound of formula (II):

(II)

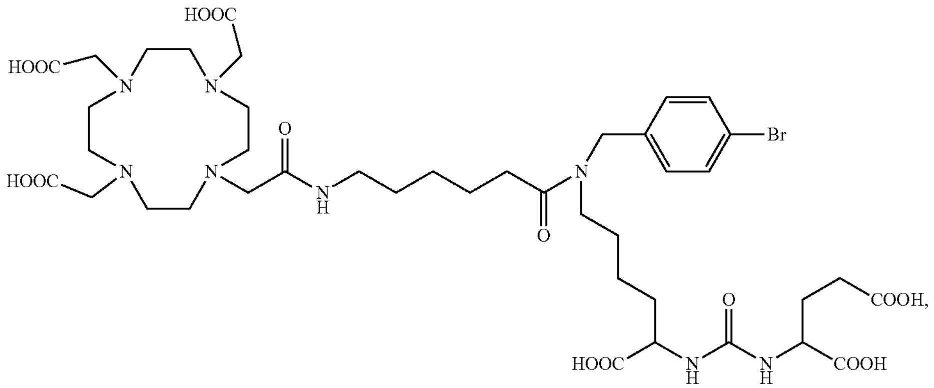

7. The compound of formula (I) according to claim 1, wherein the compound is a compound of formula (III):

(III)

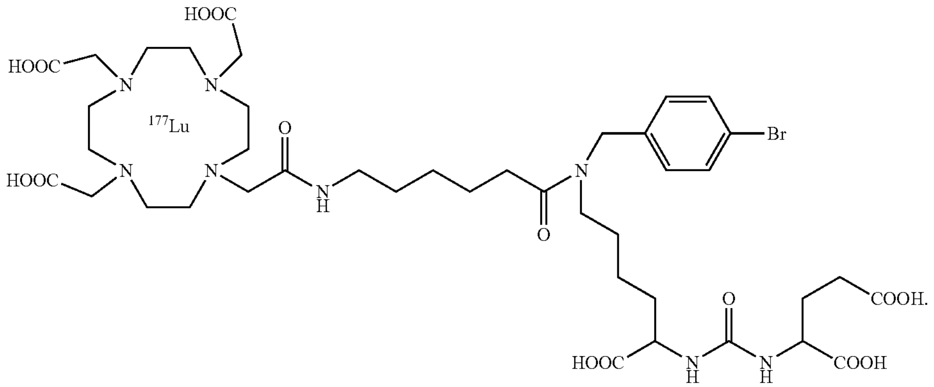

8. The compound of formula (I) according to claim 1, wherein the compound is a compound of formula (IV):

(IV)

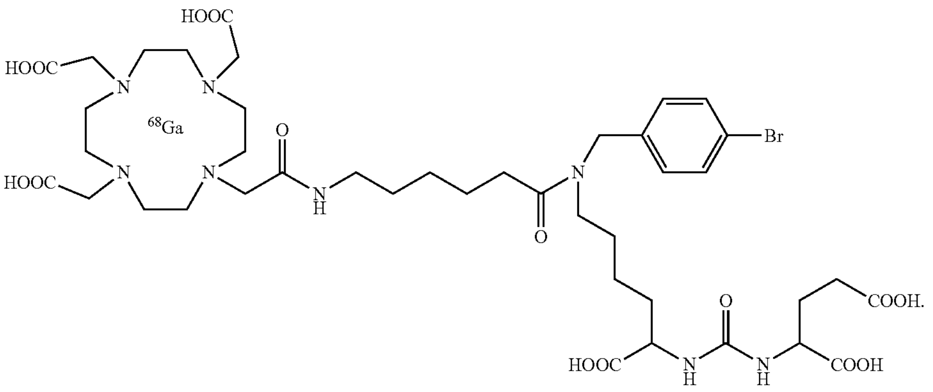

9. A pharmaceutical composition comprising a compound of formula (I) according to claim 1, and at least one pharmaceutically acceptable carrier.

10. A method for treating cancer, the method comprising contacting cancer cells with a therapeutically efficient amount of a compound of formula (I) according to claim 1.

11. A method for imaging, the method comprising contacting the cancer cells with an effective amount of the compound of formula (I) according to claim 1.

12. A method for diagnosing and/or detecting cancer cells or PSMA-expressing tumors or cells in a subject, the method comprising administering to said subject, a therapeutically efficient amount of a compound of formula (I) according to claim 1, and detecting the signal derived from the decay of the radiometal present in said compound.

13. The method of claim 10, wherein the cancer is prostate cancer.

* * * * *